United States Patent [19]

Reinhold

[11] 3,950,411

[45] Apr. 13, 1976

[54] PROCESSES FOR ASYMMETRIC CONVERSION OF 3-FLUORO-L-ALANINE AND 2-DEUTERO-3-FLUORO-L-ALANINE TO THEIR D-ISOMERS

[75] Inventor: Donald F. Reinhold, North Plainfield, N.J.

[73] Assignee: Merck & Co., Inc., Rahway, N.J.

[22] Filed: Feb. 24, 1975

[21] Appl. No.: 552,474

Related U.S. Application Data

[63] Continuation-in-part of Ser. No. 223,292, Feb. 3, 1972, Pat. No. 3,880,922.

[52] U.S. Cl............................................. 260/534 C
[51] Int. Cl.$^2$................................... C07C 99/00
[58] Field of Search ................................ 260/534 C

[56] References Cited
FOREIGN PATENTS OR APPLICATIONS 39-30152   12/1964   Japan............................. 260/534 C

OTHER PUBLICATIONS

Yuan et al., Chemical Abstracts, Vol. 54 (1960), 12096–12097.

Lettre et al., Chemical Abstracts, Vol. 68 (1968) 22229n.

Primary Examiner—Richard L. Raymond
Attorney, Agent, or Firm—Hesna J. Pfeiffer; Julian S. Levitt

[57] ABSTRACT

3-Fluoro-L-alanine is transformed by asymmetric conversion, via an intermediate L-2-(halo)-3-fluoropropionic acid, to 3-fluoro-D-alanine. The 3-fluoro-D-alanine thus obtained is a potent antibacterial agent.

8 Claims, No Drawings

PROCESSES FOR ASYMMETRIC CONVERSION OF 3-FLUORO-L-ALANINE AND 2-DEUTERO-3-FLUORO-L-ALANINE TO THEIR D-ISOMERS

This is a continuation-in-part of application Ser. No. 223,292, filed Feb. 3, 1972, now U.S. Pat. No. 3,880,922.

This invention is concerned generally with the production of 3-fluoro-D-alanine and 2-deutero-3-fluoro-D-alanine and their pharmacologically acceptable salts, which are potent antibacterial agents useful in inhibiting the growth of pathogenic bacteria of both the gram-positive and gram-negative type. More particularly, it relates to a novel asymmetric procedure whereby 3-fluoro-L-alanine or 2-deutero-3-fluoro-L-alanine are transformed to their respective D-isomers.

In accordance with one embodiment of the present invention, 3-fluoro-L-alanine is dissolved in strong (6N) aqueous hydrobromic acid or hydrochloric acid, and sodium nitrite is added portionwise to the resulting solution. The reaction is ordinarily conducted at about 0°C., under which conditions the reaction is substantially complete in about 3 hours, to produce L-2-bromo-3-fluoro-propionic acid or L-2-bromo-3-fluoro-propionic acid, respectively. The 2-halo-3-fluoro-propionic acid is conveniently recovered from the acidic reaction solution by extraction with a water-immiscible organic solvent such as methylene chloride, and evaporating the extract in vacuo; the residual L-2-halo-3-fluoro-propionic acid is purified by vacuum fractional distillation.

The L-2-bromo-3-fluoro-propionic acid, or its 2-chloro analog, is then reacted with ammonia or sodium azide. The reaction of the L-2-halo-3-fluoro-propionic acid with ammonia preferably carried out in a pressure vessel using liquid ammonia at about room temperature, under which conditions the reaction is ordinarily complete in about five days. Evaporation of the ammonia gives 3-fluoro-D-alanine which is conveniently purified by recrystallization from isopropanol-water.

The reaction of the L-2-chloro- or L-2-bromo intermediate with sodium azide is preferably carried out by bringing the reactants together in dimethylformamide, and agitating the reaction mixture at substantially room temperature, under which conditions the reaction is substantially complete in about one day; the D-2-azido-3-fluoro-propionic acid thus formed is then subjected to catalytic hydrogenation whereby the 2-azido grouping is reduced to 2-amino thereby forming 3-fluoro-D-alanine. This procedure makes possible the direct conversion of the L-isomer of 3-fluoroalanine to the D-isomer.

Similarly 2-deutero-3-fluoro-L-alanine is dissolved in strong (6N) aqueous hydrobromic acid or hydrochloric acid, sodium nitrite is added portionwise to the solution, and the resulting solution is maintained at about 0°C., for a period of about 3 hours, to produce L-2-bromo-2-deutero-3-fluoro-propionic acid or L-2-chloro-2-deutero-3-fluoro-propionic acid, respectively. The 2-halo-2-deutero-3-fluoro-propionic acid is conveniently recovered from the acidic reaction solution by extraction with a water-immiscible organic solvent such as methylene chloride, and evaporating the extract in vacuo; the residual L-2-halo-2-deutero-3-fluoro-propionic acid is purified by vacuum fractional distillation.

The L-2-bromo-2-deutero-3-fluoro-propionic acid, or its 2-chloro analog, is then reacted with ammonia or sodium azide. The reaction of the L-2-halo-2-deutero-3-fluoro-propionic acid with ammonia is preferably carried out in a pressure vessel using liquid ammonia at about room temperature, under which conditions the reaction is ordinarily complete in about five days. Evaporation of the ammonia gives 2-deutero-3-fluoro-D-alanine which is conveniently purified by recrystallization from isopropanol-water.

The reaction of the L-2-chloro- or L-2-bromo intermediate with sodium azide is preferably carried out by bringing the reactants together in dimethylformamide, and agitating the reaction mixture at substantially room temperature, under which conditions the reaction is substantially complete in about one day; the D-2-azido-2-deutero-3-fluoro-propionic acid thus formed is then subjected to catalytic hydrogenation whereby the 2-azido grouping is reduced to 2-amino thereby forming 2-deutero-3-fluoro-D-alanine. This procedure makes possible the direct conversion of the L-isomer of 2-deutero-3-fluoroalanine to the D-isomer.

As noted hereinabove, the 3-fluoro-D-alanine and 2-deutero-3-fluoro-D-alanine are potent and useful antibacterials, whereas the isomeric 3-fluoro-L-alanine and 2-deutero-3-fluoro-L-alanine (although possessing antibacterial action) are generally unwanted isomers; thus, instead of racemizing the L-isomers obtained by resolution of 3-fluoro-DL-alanine or 2-deutero-3-fluoro-DL-alanine, followed by a further resolution of the DL-mixture thus produced, these L-isomers, 3-fluoro-L-alanine and 2-deutero-3-fluoro-L-alanine, can be asymmetrically converted directly to 3-fluoro-D-alanine and 2-deutero-3-fluoro-D-alanine, respectively.

The following examples illustrate methods of carrying out the present invention, but it is to be understood that these examples are given for purposes of illustration and not of limitation.

EXAMPLE 1

3-Fluoro-L-alanine (21.4 g) is dissolved in 250 ml of 6N aqueous hydrobromic acid. The solution is cooled to 0°C. and sodium nitrite (22 g) is added in small portions with maintenance of temperature at 0°–5°C. After completing the addition, the reaction is maintained at 0°C. for 3 hours. The solution is extracted with methylene chloride which is then dried over magnesium sulfate. The methylene chloride is evaporated in vacuo. The residual L-2-bromo-3-fluoropropionic acid is purified by vacuum fractional distillation.

L-2-Bromo-3-fluoropropionic acid (3.0 g) is charged to a steel bomb and 30 ml of liquid ammonia is added. The bomb is sealed and allowed to stand at room temperature for five days. The ammonia is evaporated and the crude 3-fluoro-D-alanine is purified by recrystallization from 50% isopropanol-water.

Alternatively, the L-2-bromo-3-fluoro-propionic acid (2.0) g is dissolved in 20 ml of dimethyl formamide. Sodium azide (1.0 g) is added, and the mixture stirred at 25°C. for 24 hours. The mixture is poured into water and extracted with ether. The ether extract is washed with water and dried. About 20 ml of ethanol is added to the filtrate, and the resulting solution of D-2-azido-3-fluoro-propionic acid is reacted with hydrogen in the presence 0.5 g of 5% palladium-on-carbon. The catalyst is filtered, and the solvent is evaporated in vacuo to give crude 3-fluoro-D-alanine, which is purified by crystallization from 50% aqueous isopropanol.

EXAMPLE 2

2-Deutero-3-fluoro-L-alanine (21.4 g) is dissolved in 250 ml of 6N aqueous hydrobromic acid. The solution is cooled to 0°C., and sodium nitrite (22 g) is added in small portions with maintenance of temperature at 0°–5°C. After completing the addition, the reaction is maintained at 0°C. for 3 hours. The solution is extracted with methylene chloride which is then dried over magnesium sulfate. The methylene chloride is evaporated in vacuo. The residual L-2-bromo-2-deutero-3-fluoropropionic acid is purified by vacuum fractional distillation.

L-2-Bromo-2-deutero-3-fluoropropionic acid (3.0 g) is charged to a steel bomb and 30 ml of liquid ammonia is added. The bomb is sealed and allowed to stand at room temperature for five days. The ammonia is evaporated and the crude 2-deutero-3-fluoro-D-alanine is purified by recrystallization from 50% isopropanol-water Alternatively, the L-2-bromo-2-deutero-3-fluoropropionic acid (2.0) g is dissolved in 20 ml of dimethyl formamide. Sodium azide (1.0 g) is added, and the mixture stirred at 25°C. for 24 hours. The mixture is poured into water and extracted with ether. The ether extract is washed with water and dried. About 20 ml of ethanol is added to the filtrate, and the resulting solution of D-2-azido-2-deutero-3-fluoro-propionic acid is reacted with hydrogen in the presence 0.5 g of 5% palladium-on-carbon. The catalyst is filtered, and the solvent is evaporated in vacuo to give crude 2-deutero-3-fluoro-D-alanine, which is purified by crystallization from aqueous isopropanol.

EXAMPLE 3

3-Fluoro-L-alanine (21.4 g) is dissolved in 250 ml of 6N aqueous hydrochloric acid. The solution is cooled to 0°C. and sodium nitrite (22 g) is added in small portions with maintenance of temperature at 0°–5°C. After completing the addition, the reaction solution is maintained at 0°C. for 3 hours. The resulting solution is extracted with methylene chloride, the methylene chloride extract is dried over magnesium sulfate, and the methylene chloride is evaporated in vacuo. The residual L-2-chloro-3-fluoro-propionic acid is purified by vacuum fractional distillation.

L-2-Chloro-3-fluoropropionic acid (3.0 g) is charged to a steel bomb and 30 ml of liquid ammonia is added. The bomb is sealed and allowed to stand at room temperature for five days. The ammonia is evaporated and the crude 3-fluoro-D-alanine is purified by recrystallization from 50% isopropanol-water.

Alternatively, the L-2-Chloro-3-fluoro-propionic acid (2.0) g is dissolved in 20 ml of dimethyl formamide. Sodium azide (1.0 g) is added, and the mixture stirred at 25°C. for 24 hours. The mixture is poured into water and the D-2-azido-3-fluoro-propionic acid is catalytically hydrogenated and the product purified by recrystallization from aqueous isopropanol to give 3-fluoro-D-alanine.

EXAMPLE 4

2-Deutero-3-fluoro-L-alanine (21.4 g) is dissolved in 250 ml of 6N aqueous hydrochloric acid. The solution is cooled to 0°C. and sodium nitrite (22 g) is added in small portions with maintenance of temperature at 0°–5°C. After completing the addition, the reaction solution is maintained at 0°C. for 3 hours. The resulting solution is extracted with methylene chloride, the methylene chloride extract is dried over magnesium sulfate, and the methylene chloride is evaporated in vacuo. The residual L-2-chloro-2-deutero-3-fluoropropionic acid is purified by vacuum fractional distillation.

L-2-Chloro-2-deutero-3-fluoropropionic acid (3.0 g) is charged to a steel bomb and 30 ml of liquid ammonia is added. The bomb is sealed and allowed to stand at room temperature for five days. The ammonia is evaporated and the crude 2-deutero-3-fluoro-D-alanine is purified by recrystallization from 50% isopropanol-water.

Alternatively, the L-2-Chloro-2-deutero-3-fluoropropionic acid (2.0) g is dissolved in 20 ml of dimethyl formamide. Sodium azide (1.0 g) is added, and the mixture stirred at 25°C. for 24 hours. The mixture is poured into water and the D-2-azido-2-deutero-3-fluoro-propionic acid is catalytically hydrogenated and the product purified by recrystallization from 50% aqueous isopropanol to give 2-deutero-3-fluoro-D-alanine.

The 2-deutero-3-fluoro-L-alanine utilized as starting material in the foregoing examples is prepared as follows: A mixture of 400 ml. of ethyl ether and 240 ml. of 5N aqueous hydrochloric acid is cooled to a temperature of about −15° to −20°C. To this mixture is added, with good stirring and under a nitrogen atmosphere, about 138 grams of lump-free ethyl ethoxalyl-fluoroacetate sodium salt at a steady rate such that the temperature remains between about −15°C. and −20°C. When addition is complete, the mixture is warmed to room temperature, diluted with 240 ml. of water, and the aqueous-ethereal mixture is heated at atmospheric pressure and the ether distilled until temperature of aqueous solution reaches about 102°–105°C. The resulting aqueous solution is then heated under reflux for a period of about 4 hours. The reaction solution is cooled to room temperature, stirred with about 6 grams of activated charcoal (Darco G-60), filtered through acid-prewashed diatomaceous silica (Supercel), and the insoluble material on the filter washed with a minimum of water. The filtered solution is cooled to about 0°–5°C.; neutralized with pH control, by addition of solid lithium hydroxide hydrate (about 47 grams of LiOH·H$_2$O required) to a final pH of 6.0 to 6.5; and the resulting neutralized slurry is allowed to stand at about 0°C. for a period of approximately 15 hours. The precipitated material is recovered by filtration, washed wth a minimum of cold water, then with two 200 ml.-portions of methanol, and then with two 200 ml.-portions of acetone. The resulting material is air-dried to give about 56 grams of lithium fluoropyruvate hydrate.

To about 150 ml. of concentrated aqueous ammonium hydroxide is added, with good agitation and at room temperature, 18, 35 grams of lithium fluoro-pyruvate hydrate. The resulting suspension is heated to about 35°–37°C. (whereupon substantially all of the solid material dissolves), and the solution is maintained at that temperature for a period of about 1.5 hours. The resulting solution which may be dark in color is cooled to about 10°C., and to this cold solution is added 1.785 grams of sodium borodeuteride. The resulting solution is placed under vacuum with stirring and vigorous subsurface nitrogen flow to remove dissolved ammonia. Temperature of the solution is maintained at 10°–13°C. for a period of about 1 hour, then gradually raised to about 25°C. over a 1 hour period, and held at 28°–33°C. for a period of about 1.5 hours. The reaction solution is evaporated in vacuo at 35°C. until water distills and solution is essentially free of ammonia, and the resulting solution is then acidified with about 80 ml. of 2.5 N aqueous hydrochloric acid solution. The acidified reaction solution is stirred with about 2.5 grams of activated charcoal (Darco KB) for about 15 minutes and filtered.

The filtered solution is slowly passed through a column containing 850 ml. of acid pre-washed, strongly acidic, cation-exchange resin (Dowex 50W-X4). The column is washed with de-ionized water until the elutate is no longer acidic (about 4 liters water required), and the column is then eluted with 0.5 N aqueous ammonium hydroxide solution. The ninhydrin-postive fractions are combined, and evaporated in vacuo at a temperature not exceeding 30°C., to give about 400 ml. of an ammonia-free solution. This solution is stirred at room temperature with 2.5 grams of activated charcoal (Darco KB); the charcoal is removed by filtration, the filtered solution is again stirred with an additional 1.5 grams of activated charcoal, and the slurry is again filtered. The filtered solution is evaporated to dryness in vacuo at a temperature not exceeding 30°C. to give about 7.3 grams of crude material.

This material is dissolved in 33 ml. of water at a temperature of about 60°C; about 27 ml. of isopropanol (preheated to 60°C) is added; although crystallization occurs spontaneously on cooling, more uniform crystal growth is obtained by seeding the solution with crystals of 2-deutero-3-fluoro-DL-alanine; and the resulting mixture is cooled slowly first to room temperature and then to about 0°C. The crystalline slurry is allowed to stand at 0°C. for about 1–2 hours, the slurry is filtered, and the crystalline material on the filter is washed with two 5-ml. portions of 90% aqueous isopropanol, then with 5 ml.-portions of isopropanol, and finally with hexane. The washed material is dried in vacuo at a temperature of 50°–60°C. to give about 5.6 grams of 2-deutero-3-fluoro-DL-alanine.

The resolution of this 2-deutero-3-fluoro-DL-alanine to produce the individual L- and D- isomers is conducted as follows. The apparatus consists of three vessels, each equipped with a stirrer and a means of temperature control. The three vessels are connected in a circle by delivery lines, each of which begins in an internal filter and passed through a pump to the next vessel. Additional filters are also inserted after each pump. The first vessel in the circuit, the dissolver, is further equipped for the addition of solid 2-deutero-3-fluoro-DL-alanine benzene sulfonate and solvent. The other two vessels are the D and L crystallizers, respectively. The operation of the equipment is as follows. About 400 grams of 2-deutero-3-fluoro-DL-alanine benzenesulfonate is added to the dissolver containing two liters of absolute ethanol. The slurry is equilibrated at 25°C. for one hour and then pumping is started to the L-crystallizer. When the volume in the L-crystallizer reaches 500 ml., the pump between the L and D-crystallizers is started, and the rate is adjusted to maintain the 500 ml volume in the L-crystallizer. When the volume in the D-crystallizer reaches 500 ml, the pump between the the D-crystallizer and the dissolver is started, and the rate is adjusted to maintain the volume constant. An additional one liter of ethanol and 150 grams of 2-deutero-3-fluoro-DL-alanine benzenesulfonate are added to the dissolver, and the system equilibrated at 25°C. by pumping from vessel to vessel.

The L-crystallizer is then seeded with 25 grams of 2-deutero-3-fluoro-L-alanine benzenesulfonate, and the D-crystallizer with 25 grams of 2-deutero-3-fluoro-D-alanine benzenesulfonate. The temperature is then raised in the dissolver to 30°C. which develops a supersaturation in the crystallizers, which are maintained at 25°C.; the temperature difference between the dissolver and crystallizers is thus maintained at 5°C. Additional solid 2-deutero-3-fluoro-DL-alanine benzenesulfonate is added to the dissolver to maintain a solid phase. The solid phase in each of the crystallizers is maintained approximately constant by occasionally removing some of the crystalline slurry from each crystallizer. Filtration of the slurry from the L-crystallizer gives substantially pure 2-deutero-3-fluoro-L-alanine benzenesulfonate.

The 2-deutero-3-fluoro-L-alanine benzene sulfonate is removed from the L-crystallizer, is then dissolved in water, and passed through a sulfonic acid (H+ cycle) resin thereby adsorbing the amino acid on the resin. The column is washed with water, then eluted with dilute aqueous ammonia solution, the eluate is evaporated to small volume, isopropanol is added to the concentrated aqueous solution, and the crystalline material which separates is recovered by filtration and dried to give substantially pure 2-deutero-3-fluoro-L-alanine.

Various changes and modifications may be made in carrying out the present invention without departing from the spirit and scope thereof. Insofar as these changes and modifications are within the purview of the annexed claims, they are to be considered as part of this invention.

What is claimed is:

1. The process of asymmetrically converting an L-isomer, selected from the group consisting of 3-fluoro-L-alanine and 2-deutero-3-fluoro-L-alanine, to the corresponding D-isomer, which comprises reacting the said L-isomer in solution in aqueous hydrohalic acid with sodium nitrite thereby forming the corresponding L-2-halo-3-fluoro-propionic acid or L-2-deutero-2-halo-3-fluoro-propionic acid, and reacting this L-2-halo-3-fluoro-propionic acid or L-2-deutero-2-halo-3-fluoro-propionic acid (a) with ammonia; or (b) with sodium azide, thereby replacing the 2-halo substituent by 2-azido, followed by catalytic hydrogenation; to produce 3-fluoro-D-alanine or 2-deutero-3-fluoro-D-alanine.

2. The process as defined in claim 1 wherein the L-isomer is 3-fluoro-L-alanine, the aqueous hydrohalic acid is aqueous hydrobromic acid, and the intermediate L-2-bromo-3-fluoro-propionic acid thus formed is reacted with liquid ammonia to produce 3-fluoro-D-alanine.

3. The process as defined in claim 1 wherein the L-isomer is 2-deutero-3-fluoro-L-alanine, the aqueous hydrohalic acid is aqueous hydrobromic acid, and the intermediate L-2-deutero-2-bromo-3-fluoro-propionic acid thus formed is reacted with liquid ammonia to produce 2-deutero-3-fluoro-D-alanine.

4. The process which comprises reacting L-2-halo-3-fluoro-propionic acid or L-2-deutero-2-halo-3-fluoro-propionic acid (a) with ammonia; or (b) with sodium azide followed by catalytic hydrogenation; to produce 3-fluoro-D-alanine or 2-deutero-3-fluoro-D-alanine.

5. The process, as defined in claim 4, which comprises reacting the L-isomer of 2-chloro-3-fluoro-propionic acid with ammonia thereby forming the D-isomer of 3-fluoroalanine.

6. The process, as defined in claim 4, which comprises reacting the L-isomer of 2-deutero-2-bromo-3-fluoro-propionic acid with ammonia thereby forming the D-isomer of 2-deutero-3-fluoroalanine.

7. The process, as defined in claim 4, which comprises reacting L-2-bromo-3-fluoro-propionic acid in dimethylformamide with sodium azide to form D-2-deutero-2-azido-3-fluoro-propionic acid, and subjecting this azide to catalytic hydrogenation to produce 3-fluoro-D-alanine.

8. The process, as defined in claim 4, which comprises reacting L-2-deutero-2-bromo-3-fluoro-propionic acid in dimethylformamide with sodium azide to form D-2-deutero-2-azido-3-fluoro-propionic acid, and subjecting this azide to catalytic hydrogenation to produce 2-deutero-3-fluoro-D-alanine.

* * * * *